US00PP26125P3

(12) United States Plant Patent

Banuelos et al.

(10) Patent No.: US PP26,125 P3

(45) Date of Patent: Nov. 24, 2015

(54) ***POPULUS* TREE NAMED 'RRR YELLOW'**

(50) Latin Name: *Populus deltoids×Populus nigra*
Varietal Denomination: RRR Yellow

(71) Applicant: California State University Fresno, Fresno, CA (US)

(72) Inventors: Gary Banuelos, Fresno, CA (US); John Diener, Five Points, CA (US); James Prince, Chico, CA (US)

(73) Assignees: California State University, Fresno, Fresno, CA (US); RedRock Ranch, Five Points, CA (US); USDA, Washington, DC (US)

( * ) Notice: Subject to any disclaimer, the term of this patent is extended or adjusted under 35 U.S.C. 154(b) by 347 days.

(21) Appl. No.: 13/694,691

(22) Filed: Dec. 26, 2012

(65) Prior Publication Data

US 2014/0182024 P1 Jun. 26, 2014

(51) Int. Cl.
*A01H 5/00* (2006.01)

(52) U.S. Cl.
USPC ..... Plt./218
CPC ..... *A01H 5/00* (2013.01)

(58) Field of Classification Search
USPC ..... Plt./218
CPC ..... A01H 5/00
See application file for complete search history.

(56) References Cited

U.S. PATENT DOCUMENTS

| | | | |
|---|---|---|---|
| PP14,664 | P3 | 4/2004 | Wilkinson et al. |
| PP15,613 | P2 | 3/2005 | Newcombe |
| PP17,525 | P3 | 3/2007 | Meilan et al. |

OTHER PUBLICATIONS

Ohlendorf, Hoffman, Saiki, Aldrich. Embryonic mortality and abnormalities of acquatic birds; apparent impacts of selenium from irrigation drain water. Sci Total Environ. 52:49-63. 1986. USA.

Oster. Irrigation with poor quality water. Agric. Water Manag. 25: 271-297. 1994. USA.

Dudley, Ben-Gal, Lazarovitch. Drainage water reuse-biological, physical, and technological considerations for system management. J. Environ. Qual. 37:S-25-S-35. 2008. USA.

Lin, Cervinka, Pickering, Zayed, Terry. Managing selenium-contaminated agricultural drainage water by the integrated on-farm drainage management system: role of selenium volatilization. Water Res. 236: 3150-3160. 2002. USA.

Cervinka, Diener, Erickson, Finch, Martin, Menezes, Peters, Shelton. Integrated system for agricultural drainage management on irrigated farmland. Bureau of Reclamation, U.S. Department of the Interior, Final Research Report 4-FG-20-11920, 41. Sacramento, CA. 1999. USA.

Banuelos, Shannon, Ajwa, Draper, Jordahl, Licht. Tolerance of highbred poplar (populous) trees irrigated with varied levels of salt, selenium and boron. International Journal of Phytoremediation. 1:273-288, 1999. USA.

Banuelos, De Luc, Johnson. Evaluating the tolerance of young hybrid Poplar trees to waters high in salinity and boron. International Journal of Phytoremediation. 12:419-39. 2010. USA.

Banuelos, Schrale. Plants that remove Selenium from soils. California Agriculture. 19-20. 1989. USA.

*Primary Examiner* — Kent L Bell

(74) *Attorney, Agent, or Firm* — Grace Liu, Esq.

(57) ABSTRACT

A new and distinctly salt and boron tolerant poplar tree cultivar named 'RRR Yellow', is particularly distinguishable by its ability to tolerate and grow in soil with high concentrations of salt, boron and selenium. The 'RRR Yellow' cultivar was originally discovered as a naturally occuring branch sport through stringent selection of cultivated poplar trees, and potentially from isolation of a single unique sapling or sport that exhibited high levels of salt and boron tolerance necessary for survival, and then propagated.

4 Drawing Sheets

STATEMENT REGARDING FEDERALLY SPONSORED RESEARCH OR DEVELOPMENT

Selection and development of the 'RRR Yellow' poplar tree cultivar was sponsored by federal research at the USDA-ARS and supported by State of California funds in the form of grants from the California State University Fresno Agricultural Research Initiative and the California Department of Water Resources.

Latin name of the genus and species of the plant claimed: *Populus deltoids×Populus nigra.*

Cultivar denomination: 'RRR Yellow'.

BACKGROUND OF THE INVENTION

1. Field of the Invention

Poplar trees are part of the genus *Populus*, comprising many species, some of which can hybridize with other species within the same genus. The poplar tree is a fast growing tree and can grow under a variety of adverse conditions. Their aggressive root system can tap into shallow water tables and, as such, help manage the upward migration of water and soluble salts toward the soil surface. However, several negative physiological effects, e.g., osmotic effects, water stress, and ion imbalance, on poplar trees exposed to salinity may inhibit growth at the cost of carbohydrate production, decreased photosynthesis and stomatal conductance (Neuman, et al. (1996)). There is the need for a type of poplar tree that does not exhibit these negative physiological effects when exposed to salinity.

Irrigation water quality and drainage water disposal have become priority issues for irrigated agriculture in the western San Joaquin Valley of Central California, after inorganic salt contaminants, particularly selenium and boron, were reportedly responsible for waterfowl deformities (Ohlendorf et al., 1986). Evidence suggests that recycling saline water originating from agricultural drainage or from shallow ground waters is desirable over disposing of the saline water (Oster, 1994). Recycling poor quality water for irrigation may have application for more than 250,000 acres of drainage-impacted soils of the Western San Joaquin Valley, but its long-term use requires a critical evaluation that includes irrigation and irrigation delivery systems (Dudley et al., 2008). A practical water reuse strategy in Central California would require the selection of salt and boron tolerant crops and trees for use with waters high in salinity (e.g., 10 dS/m) and boron (10 mg/L) (Lin et al., 2002).

The Integrated on-Farm Drainage Management (IFDM) system expanded the idea of recycling salt-laden drainage water in agricultural systems (Cervinka et al., 1999). Within the IFDM system, trees may offer other advantages over vegetative plants because they transpire larger quantities of water, produce larger biomass, have longer life spans, are deeper rooted, promote greater ecosystem diversity, and regrow new stems after they have been cut. In previous IFDM implementations, trees, such as *Eucalyptus* spp. had been planted as border recipient plants for poor quality drainage and surface waters.

2. Description of the Relevant Prior Art

Salt and boron tolerant poplar trees have been selected from screenings occurring on simulated micro-field conditions in Parlier, Calif. (Banuelos, et al. 2010). The micro-field conditions were created by digging 1 m deep pits in Parlier, Calif. and filling the pits with soil (Banuelos, et al. 2010). Poplar trees were planted in the 1 m deep pits and irrigated with waters containing boron and increasing salt levels.

What is needed is the selection of salt and boron tolerant trees to be screened in actual adverse field conditions of the Western San Joaquin Valley.

BRIEF SUMMARY OF THE INVENTION

The present invention relates to a salt and boron tolerant hybrid cultivar of *Populus* named 'RRR Yellow'. The 'RRR Yellow' was identified from a field selection process to produce a poplar tree cultivar that is salt and boron tolerant, and can survive and readily phytomanage selenium from the soils and or groundwaters of the Western San Joaquin Valley region of California.

DETAILED BOTANICAL DESCRIPTION

Figure 1:
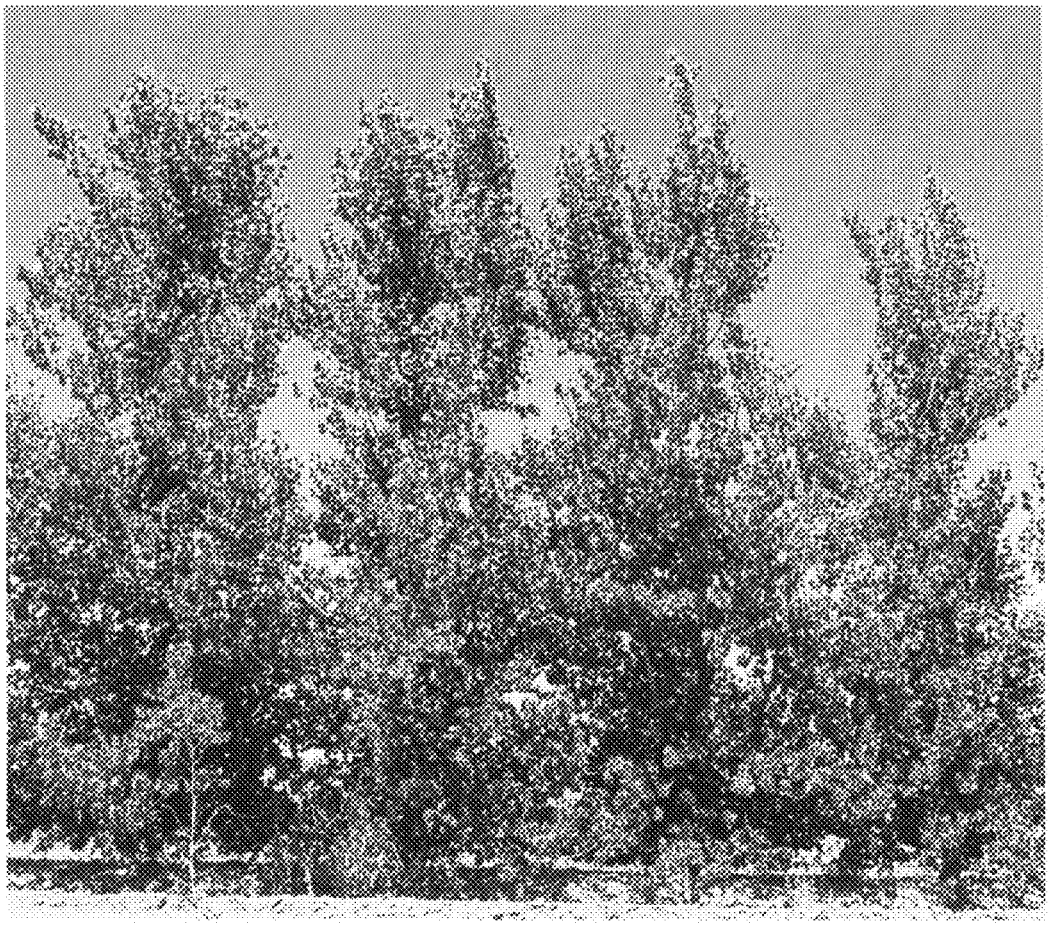
FIG. 1 shows the entire structure of three 'RRR Yellow' trees, from their trunk to their leaves.
Figure 2:
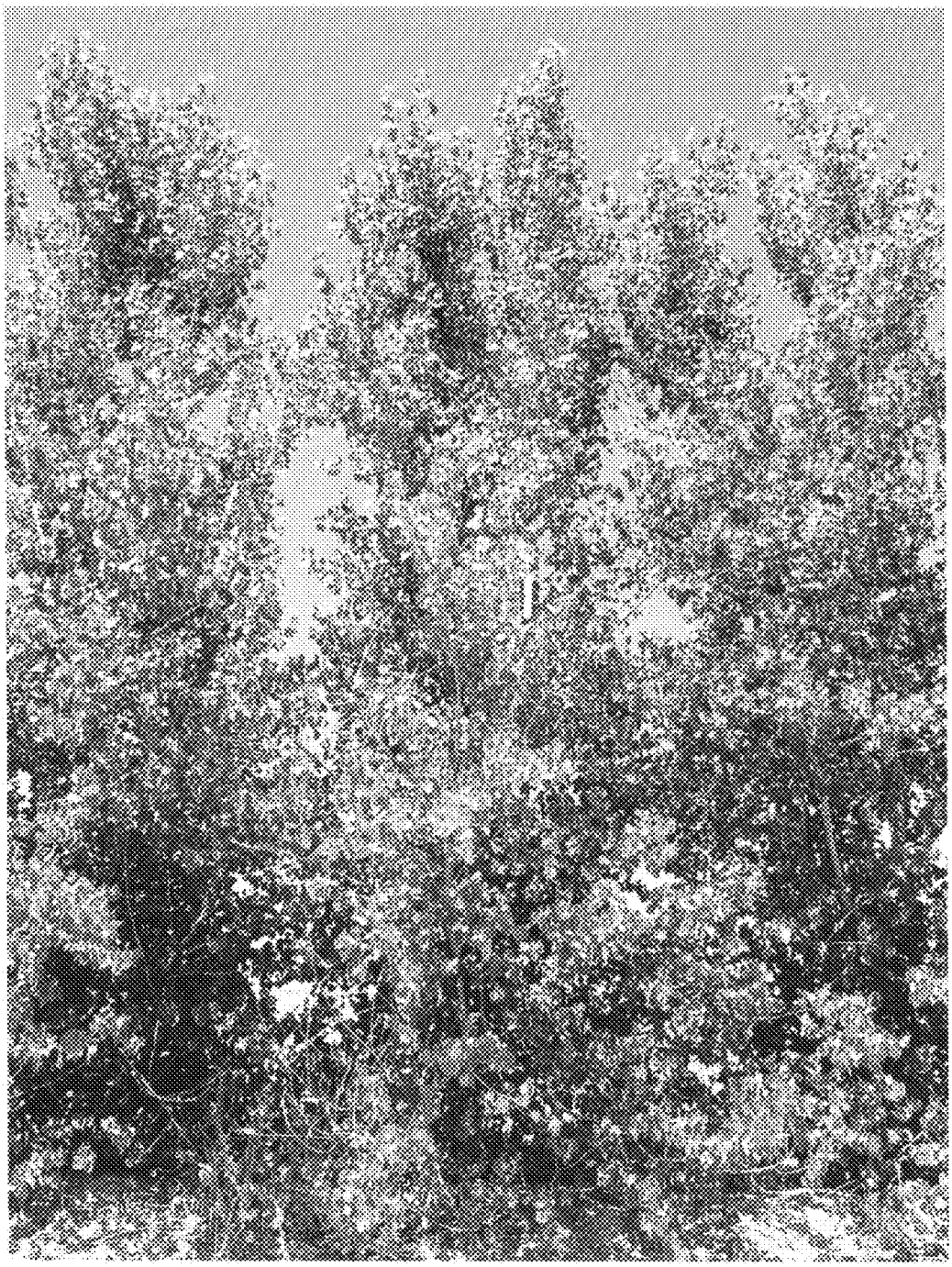
FIG. 2 shows 'RRR Yellow' trees and some of their branch structures.
Figure 3:
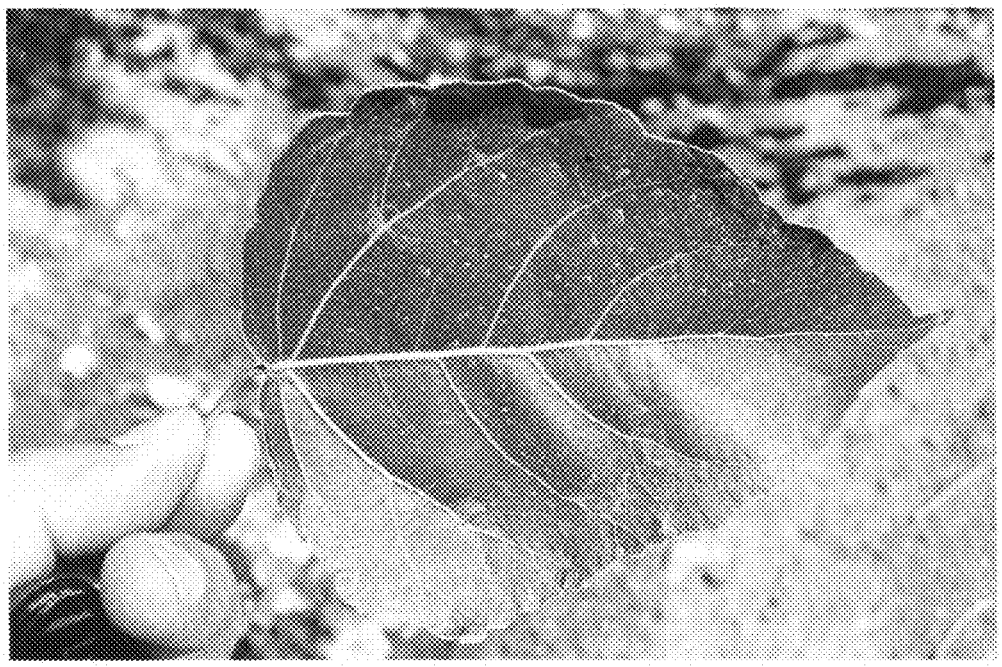
FIG. 3 shows the upper surface of a leaf from the 'RRR Yellow' tree.
Figure 4:
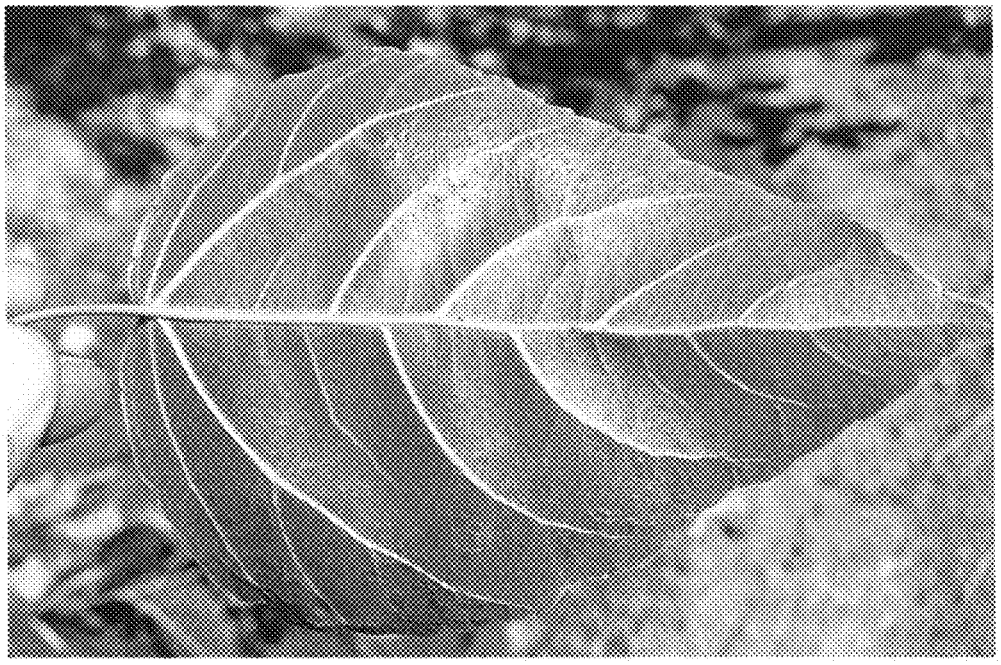
FIG. 4 shows the lower surface of a leaf from the 'RRR Yellow' tree.
Figure 5:
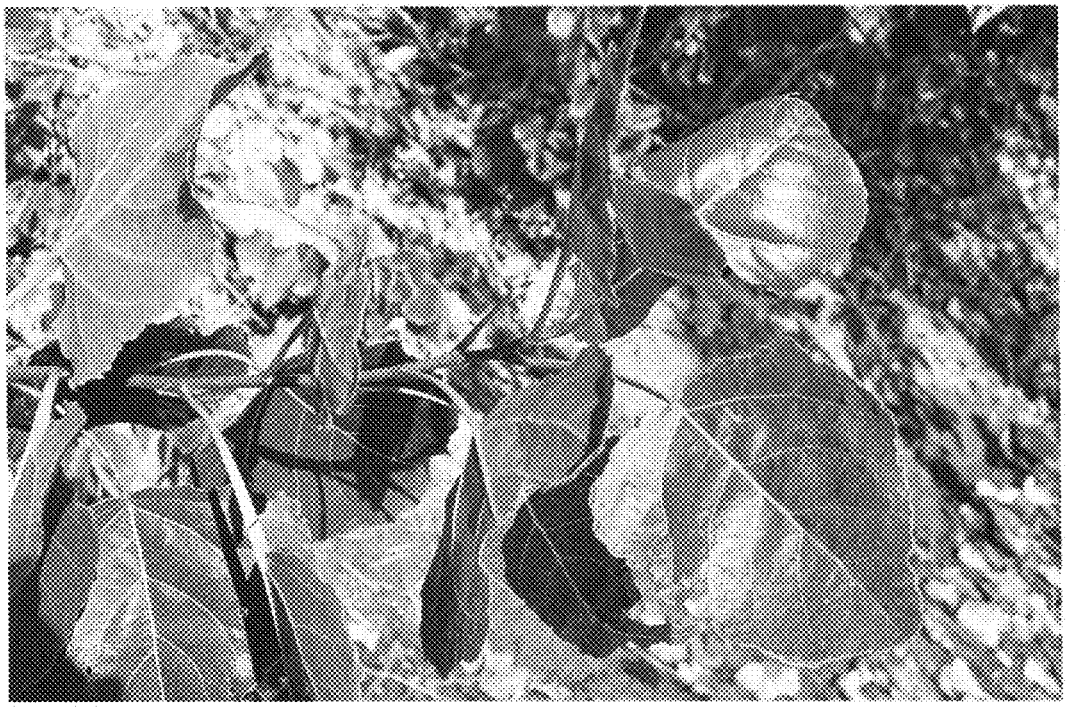
FIG. 5 shows a branch of the 'RRR Yellow' tree with leaves.

'RRR Yellow' tree is a naturally occurring branch mutation that thrives in high salt and boron soils while other poplar trees grown from cuttings of the same original tree failed to thrive in identical conditions. The 'RRR Yellow' tree was identified through a screening and cultigen selection program. 'RRR Yellow' is best described as a naturally occurring branch sport or a mutant with a uniquely expressed genotype, resulting in a phenotype allowing this unique individual to tolerate high concentrations of salt and boron. 'RRR Yellow' is a tree that was asexually propagated from one of many cuttings from one original poplar tree, which was initially selected among other for its salt and boron tolerance.

While the original tree from which the 'RRR Yellow' tree was propagated has some salt and boron tolerance, the 'RRR Yellow' tree differs from other trees grown from cuttings of the original tree in several measurable aspects. In high salt and born concentration conditions, compared to other trees grown from cuttings of the original tree, the 'RRR Yellow' tree has less leaf necrosis by about 20%, is taller in annual tree growth by about 15%, has a greater annual trunk girth growth by about 10%, and has less poplar bore insect infestation by about 15%.

1. 'RRR Yellow' Tree Identification and Selection

The 'RRR Yellow' tree was observed to thrive in extreme environmental conditions. The 'RRR Yellow' tree was identified and selected for its ability to withstand high salt and boron concentrations. Among the trees that grew from one of 80 cuttings of the original tree, the 'RRR Yellow' tree is manifestly different in its growth in high salt and high boron conditions. The selection process occurred in two steps.

In 1994, at least 200 *Populus* trees were cut biannually in Pullman, Wash. and sent to Parlier, Calif., as hardwood cuttings prior to each growing season and stored under cold storage conditions at 14° C. The *Populus* hybrid tree cuttings included: *P. nigra* (N), *P. deltoides* (D), *P. trichocarpa*×*P. nigra* (T×N), *P. trichocarpa*×*P. deltoides* (T×D), *P. deltoides*×*P. nigra* (D×N), *P. trichocarpa*×*P. maximowizcii* (T×M), *P. trichocarpa*×*P. deltoides*×*P. maximowizii* (T×D×M), and *P. trichocarpa*×*P. deltoides*×*P. nigra* (T×D×N).

In the first selection step, the *Populus* trees grown from the Washington cuttings were analyzed in microfield plots for tolerance of irrigation water containing high salt and high boron concentrations. In the second selection step, after multi-year testing, the top three performing *Populus* trees from the microfield plots were selected based on their salt and boron tolerance to undergo a further propagation and testing process in Five Points, Calif. 'RRR Yellow' tree was identified from among hundreds of trees grown from the cuttings of the selected three poplar trees as best tolerating and growing when exposed to high salt and high boron concentrations in irrigation water and in soil.

A. For the first selection process, poplar trees were grown from cuttings in microfield plots and irrigated with water having high concentrations of salt and boron.

The first selection process involved a multi-year screening study conducted in Parlier, Calif. from fall 1998 through spring 2001. The *Populus* hybrid tree cuttings were grown into young trees and those trees (<6 months) were evaluated in fall of 1998, spring and fall of 1999, spring of 2000, and spring of 2001. The *Populus* hybrid tree cuttings, measuring about 20 cm in length and about 3 cm in diameter, were planted in groups of four in 4-liter pots containing commercial potting soil mix, irrigated with good quality water, and grown under natural lighting greenhouse conditions for approximately two months prior to transplanting for both spring and fall growing seasons. All *Populus* hybrid trees were sprayed with Pentac® for spider mite control.

Ten days prior to transplanting, all planted pots were removed from the greenhouse, and the sprouted trees were hardened outside under normal weather conditions. After hardening, the sprouted *Populus* hybrid trees were transplanted into 40-liter pots containing about 58 kg of soil (Hanford fine sandy loam soil with a pH of about 7.2, electrical conductivity of about 0.9 dS/m, and boron of less than about 1 mg/L) and mixed with an equivalent of about 60 kg/ha of ammonium nitrate. Those individual planted pots were then placed into 1 m deep soil pits spaced at least 1 m part from one another.

The *Populus* hybrid trees were watered with simulated agricultural drainage waters containing high concentrations of salt and boron. Salt treatments for the recycled water were selected based in part on high salinity and boron levels typically found in Integrated on-Farm Drainage Management (IFDM) water reuse systems in the Western San Joaquin Valley of Central California. Table 1 shows the salt content of the irrigation water. The electrical conductivity (ECe) of the irrigation salt solutions was initially 10 dS/m, and 10 mg boron/L (2.7 meq/L). Salinity was increased in the irrigation water to 20 dS/m with 10 mg boron/L, and in some cases up to 30 dS/m and 10 mg boron/L. By increasing salinity incrementally, the young trees became established before being exposed to increasing salinity in the irrigation water. Control applications comprised low salinity and low boron water, <1 dS/m and <1 mg B/L.

TABLE 1

Saline Composition of Irrigation Water Used on *Populus* Hybrid Trees During Studies

| Water Salinity Measured as Electrical Conductivity (dS/m) | Ca (meq/L) | Na (meq/L) | Cl (meq/L) | $SO_4$ (meq/L) | B (meq/L) |
|---|---|---|---|---|---|
| 10 | 8 | 91 | 95 | 4 | 2.7 |
| 20 | 18 | 198 | 207 | 9 | 2.7 |
| 30 | 27 | 305 | 319 | 13 | 2.7 |

The plots containing *Populus* hybrid trees were irrigated every 2-4 days, depending on climate conditions, with an amount of water necessary to replenish water lost by evaporation and transpiration. An additional 10%-15% irrigation water was provided to account for any water lost by leaching. The estimated crop coefficient ranged from about 0.4 to about 0.7 for the young trees during one growing season. Table 2 shows the average daily high and low temperatures and total evapotranspiration losses for each respective growing season.

TABLE 2

Data Showing General Weather Conditions Experienced by *Populus* Trees

| | Total | | Average | | |
|---|---|---|---|---|---|
| | | | Air Temperature | | Solar |
| Season Dates | Precipitation (mm) | Evapo-transpiration Losses (mm) | Max (deg C.) | Min (deg C.) | radiation ($W/m^2$) |
| Fall 1998 (Oct. 6, 1998-Nov. 9, 1998) | 0.5 | 73 | 22.9 | 6.1 | 163 |
| Spring 1999 (Mar. 30, 1999-Aug. 26, 1999) | 35 | 860 | 28.7 | 12.2 | 303 |
| Fall 1999 (Sep. 13, 1999-Nov. 27, 1999) | 19.3 | 203 | 26.6 | 8.6 | 173 |
| Spring 2000 (Apr. 9, 2000-Aug. 19, 2000) | 45.7 | 796 | 31.1 | 14.0 | 311 |
| Spring 2001 (Apr. 2, 2001-Aug. 20, 2001) | 22.8 | 791 | 33.2 | 14.7 | 322 |

The harvest date for each evaluation trial was determined by the observed severity of any leaf toxicity symptoms, e.g., burning and/or and necrosis of the leaves, conditions which led to leaf drop. Due to the large number of *Populus* hybrid trees evaluated over a period of about 4 years, a general rating based upon exhibited leaf toxicity symptoms was used to indicate each tree's response to the irrigation water containing high salinity and high boron concentrations. Based upon visual observation, and subsequent estimation on the quality of the remaining leaves on the surviving *Populus* trees, at the designated end of each growing season, a general rating system was developed as follows for the boron and salt treated trees as compared to the control *Populus* trees: good (exhibited necrosis of leaf margin on remaining leaves and retained more than about 50% of its leaves), fair (exhibited moderate leaf necrosis on remaining leaves and retained between about 20% and about 50% of its leaves), and poor (exhibited severe leaf necrosis and retained less than about 20% of its leaves).

Table 3 shows the performance of the *Populus* trees planted in fall of 1998 as they were irrigated with water containing high concentrations of salt and boron. As shown in Table 3, *Populus* trees were treated for 32 days with a total of about 1200 mL water of 10 dS/m, about 900 mL water of 20 dS/m, and about 2100 mL water of 10 mg B/L. A total of about 8.8 grams of salt (including about 5 g of choloride), and about 21 mg of boron was applied to the *Populus* trees. The trees were compared to control *Populus* trees which were watered with about 6750 mL of good quality water.

TABLE 3

Results of Irrigating Poplar Trees Planted as Hardwood Cuttings in Fall of 1998 with Water Containing High Concentrations of Salt and Boron.

| Tree Designation | Parentage | Performance |
|---|---|---|
| 347-14 | TD x N | Good |
| 14-129 | D | Poor |
| 93-968 | T | Poor |
| 184-408 | T x D | Poor |
| 184-411 | T x D | Poor |
| 195-529 | T x D | Poor |
| 23-91 | T x D | Poor |
| 23-96 | T x D | Poor |
| 52-225 | T x D | Poor |
| 52-229 | T x D | Poor |
| 262-4 | T x M | Poor |
| 272-239 | T x M | Poor |
| 282-189 | T x M | Poor |
| 306-49 | T x N | Poor |
| 310-84 | T x N | Poor |
| 310-85 | T x N | Poor |
| 353-273 | T x TD | Poor |
| 233-3 | TD x M | Poor |
| Eridano | D x M | Poor |

Table 4 shows the performance of the *Populus* trees planted in spring of 1999 as they were irrigated with water containing high concentrations of salt and boron. As shown in Table 4, *Populus* trees were treated for 148 days with a total of about 2250 mL water of 10 dS/m, about 8750 mL water of 20 dS/m, about 1800 mL water of 30 dS/m, and about 12,800 mL water of 10 mg B/L. A total of about 161 grams of salt (including about 92 g of chloride), and about 120 mg of boron was applied to the *Populus* trees. The trees were compared to control *Populus* trees, which were watered with about 26,250 mL of good quality water.

TABLE 4

Results of Irrigating Poplar Trees Planted as Hardwood Cuttings in Spring of 1999 with Water Containing High Concentrations of Salt and Boron.

| Tree Designation | Parentage (Tree Designation) | Performance |
|---|---|---|
| 13-308 | N | Good |
| 13-366 | D x N | Good |
| Simplot Alkaline | D x N | Good |
| 311-93 | T x N | Good |
| Tassman | D x N | Fair |
| 345-1 | T x N | Fair |
| 12-106 | T | Poor |
| 91-568 | T | Poor |
| 13-17 | N | Poor |
| 14-66 | D x N | Poor |
| 184-40 | T x D | Poor |
| 184-402 | T x D | Poor |
| 23-91 | T x D | Poor |
| 272-97 | T x D | Poor |
| 272-98 | T x M | Poor |
| 281-181 | T x M | Poor |
| 286-74 | T x M | Poor |
| 286-69 | TD x M | Poor |
| 310-87 | T x N | Poor |
| 346-12 | TD x N | Poor |
| 347-13 | TD x N | Poor |
| 347-14 | TD x N | Poor |

Table 5 shows the performance of the *Populus* trees planted in fall of 1999 as they were irrigated with water containing high concentrations of salt and boron. As shown in Table 5, *Populus* trees were treated for 75 days with a total of about 12,400 mL water of 10 dS/m, about 900 mL water of 20 dS/m, about 13,300 mL water of 30 dS/m, and about 12,800 mL water of 10 mg B/L. A total of about 91 grams of salt (including about 48 g of chloride), and about 133 mg of boron was applied to the *Populus* trees. The trees were compared to control *Populus* trees which were watered with about 18,000 mL of good quality water (less than 1 dS/m).

TABLE 5

Results of Irrigating Poplar Trees Planted as Hardwood Cuttings in Fall of 1999 with Water Containing High Concentrations of Salt and Boron.

| Tree Designation | Parentage | Performance |
|---|---|---|
| 304-22 | T x N | Good |
| 315-131 | T x N | Good |
| 302-4 | T x N | Poor |
| 302-5 | T x N | Poor |
| 302-6 | T x N | Poor |
| 303-11 | T x N | Poor |
| 303-12 | T x N | Poor |
| 304-21 | T x N | Poor |
| 304-23 | T x N | Poor |
| 305-31 | T x N | Poor |
| 305-32 | T x N | Poor |
| 305-33 | T x N | Poor |
| 306-41 | T x N | Poor |
| 306-42 | T x N | Poor |
| 307-51 | T x N | Poor |
| 308-61 | T x N | Poor |
| 313-111 | T x N | Poor |
| 313-112 | T x N | Poor |
| 313-113 | T x N | Poor |
| 314-121 | T x N | Poor |
| 314-122 | T x N | Poor |
| 314-123 | T x N | Poor |
| 315-132 | T x N | Poor |
| 316-141 | T x N | Poor |
| 318-161 | T x N | Poor |
| 318-162 | T x N | Poor |

Table 6 shows the performance of the *Populus* trees planted in spring of 2000 as they were irrigated with water containing high concentrations of salt and boron. As shown in Table 6, *Populus* trees were treated for 132 days with a total of about 4500 mL water of 10 dS/m, about 6800 mL water of 20 dS/m, about 5400 mL water of 30 dS/m, and about 16,700 mL water of 10 mg B/L. A total of about 220 grams of salt (including about 126 g of chloride), and about 167 mg of boron was applied to the *Populus* trees. The trees were compared to control *Populus* trees which were watered with about 26,200 mL of good quality water.

TABLE 6

Results of Irrigating Poplar Trees Planted as Hardwood Cuttings in Spring of 2000 with Water Containing High Concentrations of Salt and Boron.

| Tree Designation | Parentage | Performance |
|---|---|---|
| 13-366 | D x N | Good |
| Simplot Alkaline | D x N | Good |
| 302-1 | T x N | Good |
| 302-4 | T x N | Good |
| 303-14 | T x N | Good |
| 304-22 | T x N | Good |
| 304-26 | T x N | Good |
| 305-35 | T x N | Good |
| 309-71 | T x N | Good |
| 309-72 | T x N | Good |
| 311-93 | T x N | Good |
| 345-1 | TD x N | Good |
| 347-14 | TD x N | Good |
| 13-308 | N | Fair |
| 315-131 | T x N | Fair |
| 315-135 | T x N | Fair |
| 14-71 | D | Poor |
| Tassman | D x N | Poor |
| 303-13 | T x N | Poor |
| 304-25 | T x N | Poor |
| 305-34 | T x N | Poor |
| 306-41 | T x N | Poor |
| 306-42 | T x N | Poor |
| 306-44 | T x N | Poor |
| 306-45 | T x N | Poor |
| 312-101 | T x N | Poor |

Table 7 shows the performance of the *Populus* trees planted in spring of 2001 as they were irrigated with water containing high concentrations of salt and boron. As shown in Table 7, *Populus* trees were treated for 122 days with a total of about 800 mL of good quality water, 6800 mL water of 10 dS/m, about 13,800 mL water of 20 dS/m, about 20,600 mL water of 10 mg B/L. A total of about 220 grams of salt (including about 123 g of chloride), and about 206 mg of boron was applied to the *Populus* trees. The trees were compared to control *Populus* trees which were watered with about 45,700 mL of good quality water.

TABLE 7

Results of Irrigating Poplar Trees Planted as Hardwood Cuttings in Spring of 2001 with Water Containing High Concentrations of Salt and Boron.

| Tree Designation | Parentage | Performance |
|---|---|---|
| 313-114 | T x N | Good |
| 314-124 | T x N | Fair |
| 302-1 | T x N | Poor |
| 302-4 | T x N | Poor |
| 303-14 | T x N | Poor |
| 304-24 | T x N | Poor |
| 304-26 | T x N | Poor |
| 304-27 | T x N | Poor |

TABLE 7-continued

Results of Irrigating Poplar Trees Planted as Hardwood Cuttings in Spring of 2001 with Water Containing High Concentrations of Salt and Boron.

| Tree Designation | Parentage | Performance |
|---|---|---|
| 304-28 | T x N | Poor |
| 305-35 | T x N | Poor |
| 306-43 | T x N | Poor |
| 306-47 | T x N | Poor |
| 306-448 | T x N | Poor |
| 309-71 | T x N | Poor |
| 309-72 | T x N | Poor |
| 311-93 | T x N | Poor |
| 313-115 | T x N | Poor |
| 315-132 | T x N | Poor |
| 316-143 | T x N | Poor |
| 317-152 | T x N | Fair |
| 317-153 | T x N | Poor |
| 317-154 | T x N | Poor |

B. For the second selection process, three selected poplar tree were each cut multiple times and the cuttings were planted in salt and boron-laden soils in the Western San Joaquin Valley. 'RRR Yellow' was the best performing tree from among hundreds of trees.

Three of the top *Populus* trees rated as "Good" performers during the microfield studies were selected for a second selection process because they were repeatedly the heartiest trees during the first selection process. These selected trees are: 13-366, 345-1, and 347-14. In spring of 2006, 80 cuttings were taken respectively from each of these selected three original trees, and planted in the Western San Joaquin Valley in Central California. Each cutting was planted 3 m apart and replicated four times within one block; there were a total of 20 blocks running north and south. After 6 years of growth under these adverse conditions (described below), the field selection showed that 'RRR Yellow', propagated from a cutting of tree 13-366 (D×N), was the best performer in all tested blocks. Evidence of this was observed through greater leaf biomass, greater height, and less necrotic leaves near the latter part of each growing season. As stated earlier, in high salt and born concentration conditions, compared to other trees grown from cuttings of the original tree 13-366, the 'RRR Yellow' tree has less leaf necrosis by about 20%, is taller in annual tree growth by about 15%, has a greater annual trunk girth growth by about 10%, and has less poplar bore insect infestation by about 15%.

The environment in Five Points, Calif. is very dry, hot, and exposed to high light intensity. The average summer (June-August) temperature in Five Points, Calif. ranges from a high of approximately 35 degrees C. during the day to a low of approximately 16 degrees C. at night. The average winter temperature (January and February) in Five Points, Calif. ranges from a high of approximately 12 degrees C. during the day to a low of approximately 3 degrees C. at night. The relative humidity ranges from approximately 28% to approximately 70% in the summer (June-August), and approximately 70% to approximately 95% in the winter (January and February). Horizontal solar radiation averages approximately 8 $kWh/m^2/d$ in July with an annual total ranging from approximately 1.8 $MWh/m^2$ to approximately 2.0 $MWh/m^2$. There is virtually no rainfall for four months from May through September, and evapotranspiration (ETo) remains high with daily rates of approximately 7 mm (7 $L/m^2/d$).

Five Points, Calif. has clay soils, containing high concentrations of salt ($Na_2SO_4$, NaCl, $CaCl_2$, $Na_2SeO_4$, $CaSO_4$, $Na_2B_4O_5(OH)_4$, and $CaB_3O_4(OH)_3$) and boron. The soil composition is classified as an Oxalis silty clay loam (fine montmorillonitic, thermic Pachic Haploxeral) with a well-developed salinity profile. Soil salinity varies from approximately 4 dS/m to approximately 8 dS/m, while soluble boron varies from approximately 4 mg/L to approximately 7 mg/L. The top 30 cm of soil contains between approximately 2 μg Se/g and approximately 4 μg Se/g of total selenium, and the extractable selenium concentrations range between approximately 0.8 μg Se/mL and approximately 1.2 μg Se/mL. The presence of poor quality shallow groundwater underneath the trees (fluctuates between 1 m and 3 m from soil surface) contributed to additional salt and boron stress for the trees. Periodic groundwater sampling showed that EC and B ranged from 10 dS/m to 18 dS/m and 10 mg/L to 18 mg/L, respectively.

The 'RRR Yellow' tree tolerates the high salt and high boron soil conditions, as well as the climate conditions, very well. The 'RRR Yellow' tree is still alive and growing well in Five Points, Calif. The 'RRR Yellow' tree has been successfully reproduced asexually from planting at least 50 hardwood cuttings in Five Points, Calif. from 2008-present (about 10 trees per year), and from planting 10 hardwood cuttings in heavy metal contaminated soils at the University of Zurich in Switzerland in 2009. The approximately 60 reproduced trees are still alive.

2. 'RRR Yellow' Cultivar Specification

The following detailed description sets forth the distinctive characteristics of the 'RRR Yellow' poplar tree. The data which define these characteristics were collected from a 6-year old tree growing in Five Points, Calif. The comparison "typical" tree were planted from a cutting of the same original tree 13-366 at the same time as 'RRR Yellow' and is growing in the same conditions. Color references are to The Royal Horticulture Society Color Chart (2001 edition).

Classification: *Populus deltoides×Populus nigra.*

Common name: Poplar.

Tree:

*'RRR Yellow' vigor.*—Moderate.

*'RRR Yellow' shape.*—Upright, columnar; annual growth 1.3 m.

*'RRR Yellow' height of the entire tree including crown.*—Approximately 10 meters to 12 meters.

*'RRR Yellow' tree spread.*—10 m (typical tree spread: 8 m).

Trunk:

*'RRR Yellow' size.*—Original tree, caliper about 45 cm at 0.5 m from ground.

*'RRR Yellow' diameter at 6 years of age measured at 2 m off the ground.*—42.0 cm (typical tree diameter at 6 years of age measured at 2 m off the ground: 32.6 cm).

*'RRR Yellow' height to first limb.*—1.9 m.

*'RRR Yellow' growth habit.*—Erect excurrent branching.

*'RRR Yellow' growth rate.*—1.3 m/annually.

*'RRR Yellow' bark color.*—Grey brown 199B and grey orange N170B.

*'RRR Yellow' bark texture.*—Rough on lower 1 meter and smooth beyond.

*'RRR Yellow' branches.*—Emerge at an angle of between 30 degrees and 60 degree from trunk.

*'RRR Yellow' branching habit.*—Dominant main stem with ascending excurrent branching.

*'RRR Yellow' color.*—Two year old shoot bark color, grey green 198A. One year-old lateral branches, grey green 195B.

*'RRR Yellow' crotch angle.*—40 degrees to 45 degrees.

*'RRR Yellow' internode length.*—Average internode length on one-year shoot 6 cm (range 3 to 7 cm).

*'RRR Yellow' branch length of first upright branch.*—7.6 m (typical branch length: 5.9 m).

*'RRR Yellow' branch diameter.*—17.9 (typical branch diameter: 13.9 cm).

*'RRR Yellow' mature leaves.*—'RRR Yellow' Length: Range 5 cm to 10 cm; average 7.6 cm. 'RRR Yellow' Width: Range of 6 cm to 12 cm; average 8.8 cm. 'RRR Yellow' Petiole: 30 mm to 45 mm in length; average 38 mm; diameter 1 mm to 3 mm. Color of petiole is red 44 C on upper surface, and yellow green 153A on lower surface. 'RRR Yellow' Shape: Broadly ovate. 'RRR Yellow' Color of upper surface: green 139A. 'RRR Yellow' Color of lower surface: dull green N138B. 'RRR Yellow' Texture: Upper surface: very smooth, glossy sheen. Lower surface: smooth, dull, leathery. 'RRR Yellow' leaf apex: Accuminate (typical leaf apex: Accuminate). 'RRR Yellow' leaf margin: Serrate/Crenate (typical leaf margin: Dentate/Crenate). 'RRR Yellow' leaf base: Truncate (typical leaf base: Truncate).

*'RRR Yellow' leaf buds.*—Length: approximately 7 mm, narrow. Color: color grey orange 171A and yellow green 144B. Shape: Narrow ovate, 4 mm at base and pointed at tip. Bud scale shape: ovate. Bud scale number: 8-10.

*'RRR Yellow' flowers.*—None.

*'RRR Yellow' pest and disease resistance.*—No known pest or disease resistance.

What is claimed is:

1. A new and distinct salt and boron tolerant poplar tree named 'RRR Yellow', as substantially illustrated and described herein.

* * * * *